United States Patent [19]

Bell

[11] 4,452,988

[45] * Jun. 5, 1984

[54] 1-ETHENYL-6-(4-PHENYL)-3,4,9,9A-TETRAHYDRO-9A-METHYL-6H-NAPTHO[2,3-C]PYRAZOLES

[75] Inventor: Malcolm R. Bell, East Greenbush, N.Y.

[73] Assignee: Sterling Drug Inc., New York, N.Y.

[*] Notice: The portion of the term of this patent subsequent to Sep. 14, 1999 has been disclaimed.

[21] Appl. No.: 447,010

[22] Filed: Dec. 6, 1982

[51] Int. Cl.$^3$ .............................................. C07D 231/54
[52] U.S. Cl. ...................................... 548/369; 568/374
[58] Field of Search ............................................ 548/369

[56] References Cited

U.S. PATENT DOCUMENTS

| 4,307,102 | 12/1981 | Bell | 548/369 |
| 4,349,558 | 9/1982 | Bell | 548/369 |
| 4,349,559 | 9/1982 | Bell et al. | 548/369 |

FOREIGN PATENT DOCUMENTS 58841  9/1982  European Pat. Off. .

*Primary Examiner*—Donald G. Daus
*Assistant Examiner*—Chabic Kalita
*Attorney, Agent, or Firm*—Thomas L. Johnson; B. Woodrow Wyatt; Paul E. Dupont

[57] ABSTRACT

Novel compounds, 1-ethenyl-6-(4-R'-phenyl)-3,4,9,9a-tetrahydro-9a-methyl-6H-naphtho[2,3-c]pyrazoles, wherein R' is hydrogen or fluoro, are useful as intermediates in the preparation of anti-inflammatory agents.

3 Claims, No Drawings

1-ETHENYL-6-(4-PHENYL)-3,4,9,9A-TETRAHYDRO-9A-METHYL-6H-NAPTHO[2,3-C]PYRAZOLES

The present invention relates to novel polycyclic fused ring pyrazole compounds useful as intermediates.

In particular, the invention relates to compounds of the formula:

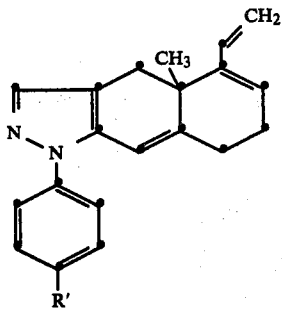

I wherein R' is hydrogen or fluoro.

RELATED PATENTS AND APPLICATION

Bell U.S. Pat. No. 4,349,558, issued Sept. 14, 1982 (application Ser. No. 235,440, filed February 19, 1981) discloses the compound of formula I where R' is fluoro and its use as an intermediate in preparing phenanthro[2,3-c]-pyrazole derivatives useful as anti-inflammatory agents.

Bell U.S. Pat. No. 4,307,102, issued Dec. 22, 1981 (application Ser. No. 235,435, filed February 19, 1981) discloses the compound of formula I where R' is fluoro and its use as an intermediate in preparing 8-(4-fluorophenyl)-2,3,4,4a,5,6,11,11a-octahydro-11a-methyl-4-(2-pyridinyl)-8H-phenanthro[2,3-c]pyrazole, useful as an anti-inflammatory agent.

Bell and Herrmann U.S. Pat. No. 4,349,559, issued Sept. 14, 1982 (application Ser. No. 236,216, filed Feb. 19, 1981) discloses the compounds of formula I and their use as intermediates in preparing spiro-2H-indene-[2,3']-3H-pyrazolo[4'',5'':7',6']naphtho[2,1-b]pyran-1,3-dione compounds, useful as anti-inflammatory agents.

Bell and Herrmann U.S. Patent Application, Ser. No. 339,116, filed Jan. 13, 1982 (continuation-in-part of application Ser. No. 236,215, filed Feb. 19, 1981, now abandoned) discloses the compounds of formula I and their use as intermediates in preparing 8-(4-R'-phenyl)-4a,5,6,8,11,11a-hexahydro-11a-methylspiro[[1]-benzopyrano[5,6-f]indazole-3(2H),5'(2'H)-pyrimidine]-2',4',6'-(1'H-3'H)trione compounds, useful as anti-inflammatory agents.

DETAILED DESCRIPTION INCLUSIVE OF PREFERRED EMBODIMENTS

The novel intermediates of formula I are prepared from a known starting material, 5-ethenyl-4,4a,7,8-tetrahydro-4a-methyl-2(3H)-naphthalenone (cf. Bell et al. U.S. Pat. No. 4,157,349, June 5, 1979) in accordance with the following reactions:

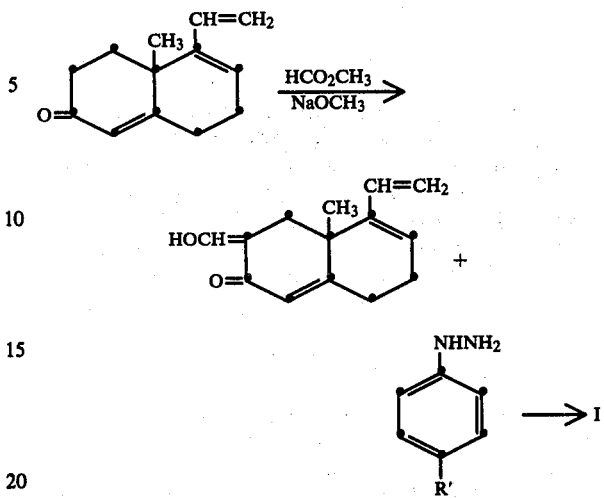

The trienone starting material is reacted with methyl formate in the presence of sodium methoxide in an inert solvent such as tetrahydrofuran to afford 5-ethenyl-3-hydroxymethylene-4,4a,7,8-tetrahydro-4a-methyl-2(3H)-naphthalenone, and the latter is then reacted with phenylhydrazine or 4-fluorophenylhydrazine or an acid-addition salt thereof in the presence of acetic acid to give a compound of formula I.

EXAMPLE 1

(a)

5-Ethenyl-3-hydroxymethylene-4,4a,7,8-tetrahydro-4a-methyl-2(3H)-naphthalenone.

A solution of 50.0 g (0.265 mol) of 5-ethenyl-4,4a,7,8-tetrahydro-4a-methyl-2(3H)-naphthalenone in 350 mL of tetrahydrofuran was cooled to −5° C. in an ice-methanol bath and stirred under nitrogen while 57.2 g (1.06 mol) of sodium methoxide was added. The resulting mixture was stirred for 30 min at −5° C. and then a solution of 114 mL (1.85 mol) of methyl formate in 100 mL of tetrahydrofuran was added slowly. The mixture was stirred overnight at room temperature and then poured onto a mixture of ice-water (1500 mL) and 6N hydrochloric acid (265 mL). The product was extracted with ether and the combined extracts were washed with water. The dried extract was dried over anhydrous magnesium sulfate and concentrated in vacuo to afford an oil. This oil was triturated with hexane (4×250 mL) and the combined triturates were dried over magnesium sulfate and concentrated in vacuo to afford 55.37 g of a red oil, consisting essentially of the above-entitled compound as established by proton NMR (PMR) spectral data.

(b)

1-Ethenyl-6-(4-fluorophenyl)-3,4,9,9a-tetrahydro-9a-methyl-6H-naphtho[2,3-c]pyrazole (I; R'=F).

4-Fluorophenylhydrazine hydrochloride (45.85 g, 0.282 mol) and sodium acetate (23.14 g, 0.282 mol) were added to a solution of 55.37 g (0.256 mol) of the product obtained in part (a) above in 225 mL of glacial acetic acid. The mixture was stirred overnight at room temperature and then concentrated in vacuo to afford a semi-solid. This material was suspended in ether (1 L) and filtered to remove sodium chloride. The ether filtrate was washed with water (4×250 mL), saturated sodium bicarbonate (until weakly basic) and saturated sodium chloride (100 mL). The extract was dried over anhydrous magnesium sulfate, decolorized with charcoal and concentrated in vacuo to afford an oil. This oil was triturated with 1:2 ether-hexane (3×750 mL) to afford 69.58 g of a dark brown oil. An analytical sample was prepared by using high-performance liquid chromatography with 1:3 ether-hexane as solvent. The resulting yellow oil was triturated with pentane to afford 1-ethenyl-6-(4-fluorophenyl)-3,4,9,9a-tetrahydro-9a-methyl-6H-naphtho[2,3-c]-pyrazole as a yellow solid, m.p. 70°–72° C., with a consistent PMR spectrum.

EXAMPLE 2

1-Ethenyl-6-phenyl-3,4,9,9a-tetrahydro-9a-methyl-6H-naphtho[2,3-c]pyrazole (I; R'=H).

A mixture of 17.92 g of 5-ethenyl-4,4a,7,8-tetrahydro-4a-methyl-2(3H)-naphthalenone (Example 1a), 13.2 g of phenylhydrazine hydrochloride and 7.49 g of sodium acetate in 100 ml of glacial acetic acid was stirred at room temperature overnight. The mixture was then concentrated in vacuo, diluted with about 400 ml of methylene dichloride and filtered to remove sodium chloride. The filtrate was washed with water, saturated sodium bicarbonate solution (until weakly basic) and saturated sodium chloride solution, and dried over anhydrous magnesium sulfate with activated carbon added. The suspension was filtered and concentrated to an oil, which was triturated with 250 ml of ether and 300 ml of hexane, decanted and triturated again with ether and hexane. The combined extracts were filtered through a pad of magnesium sulfate and concentrated to a brown oil, 19.09 g of I (R'=H) with PMR spectrum consistent with the assigned structure.

The compounds of Examples 1 and 2 were reacted with various dienophiles to form compounds useful as anti-inflammatory agents as described in U.S. Pat. Nos. 4,307,102, 4,349,558 and 4,349,559, cited above, the disclosures of which are incorporated herein by reference.

I claim:

1. A compound having the formula

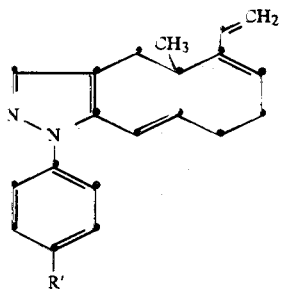

wherein R' is hydrogen or fluoro.

2. 1-Ethenyl-6-(4-fluorophenyl)-3,4,9,9a-tetrahydro-9a-methyl-6H-naphtho[2,3-c]pyrazole, according to claim 1.

3. 1-Ethenyl-6-phenyl-3,4,9,9a-tetrahydro-9a-methyl-6H-naphtho[2,3-c]pyrazole, according to claim 1.